(12) United States Patent
Geiser et al.

(10) Patent No.: US 11,505,827 B2
(45) Date of Patent: Nov. 22, 2022

(54) SYSTEMS AND METHODS FOR DETERMINING GENETIC DATA

(71) Applicants: Roche Sequencing Solutions, Inc., Pleasanton, CA (US); LIFE TECHNOLOGIES CORPORATION, Carlsbad, CA (US)

(72) Inventors: Timothy Geiser, San Mateo, CA (US); Randall Davis, Pleasanton, CA (US); Roger Chen, Saratoga, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 96 days.

(21) Appl. No.: 16/351,456

(22) Filed: Mar. 12, 2019

(65) Prior Publication Data

US 2019/0292591 A1   Sep. 26, 2019

Related U.S. Application Data

(62) Division of application No. 14/355,203, filed as application No. PCT/US2012/063099 on Nov. 1, 2012, now Pat. No. 10,260,093.

(60) Provisional application No. 61/554,815, filed on Nov. 2, 2011.

(51) Int. Cl.
| | |
|---|---|
| *C12M 1/34* | (2006.01) |
| *C12Q 1/6874* | (2018.01) |
| *C12Q 1/6869* | (2018.01) |
| *B82Y 15/00* | (2011.01) |

(52) U.S. Cl.
CPC ........... *C12Q 1/6874* (2013.01); *B82Y 15/00* (2013.01); *C12Q 1/6869* (2013.01)

(58) Field of Classification Search
USPC ............... 435/6.1, 6.11, 91.1; 436/94, 501; 536/23.1, 24.3, 24.33
See application file for complete search history.

(56) References Cited

U.S. PATENT DOCUMENTS

| | | | | |
|---|---|---|---|---|
| 8,845,880 | B2 * | 9/2014 | Davis | B82Y 15/00 205/792 |
| 9,121,059 | B2 | 9/2015 | Davis | |
| 10,260,093 | B2 * | 4/2019 | Geiser | B82Y 15/00 |

(Continued)

FOREIGN PATENT DOCUMENTS

| | | |
|---|---|---|
| WO | 2011097028 A1 | 8/2011 |
| WO | 2012088339 A2 | 6/2012 |
| WO | 2012088341 A2 | 6/2012 |

OTHER PUBLICATIONS

Nichols et al., A universal nucleoside for use at ambiguous sites in DNA primers. Nature, 369, 492-493, 1994.*

(Continued)

*Primary Examiner* — Frank W Lu
(74) *Attorney, Agent, or Firm* — FisherBroyles, LLP; Victoria L. Boyd

(57) ABSTRACT

Systems and methods of polynucleotide sequencing are provided. Systems and methods optimize control, speed, movement, and/or translocation of a sample (e.g., a polynucleotide) within, through, or at least partially through a nanopore or a type of protein or mutant protein in order to accumulate sufficient time and current blocking information to identify contiguous nucleotides or plurality of nucleotides in a single-stranded area of a polynucleotide.

11 Claims, 1 Drawing Sheet

(56) References Cited

U.S. PATENT DOCUMENTS

| | | |
|---|---|---|
| 2007/0190542 A1 | 8/2007 | Ling |
| 2010/0035260 A1 | 2/2010 | Olasagati |
| 2010/0243449 A1 | 9/2010 | Oliver |
| 2010/0297644 A1 | 11/2010 | Kokoris |
| 2012/0160681 A1 | 6/2012 | Davis |
| 2012/0160688 A1 | 6/2012 | Davis |
| 2013/0203610 A1* | 8/2013 | Meller ............... C12Q 1/6874 506/6 |
| 2014/0034517 A1* | 2/2014 | Akeson .................. C25B 3/29 205/792 |

OTHER PUBLICATIONS

Benner, et al., Sequence-specific detection of individual DNA polymerase complexes in real time using a nanopore, Nature Nanotechnology, vol. 2, No. 11, pp. 718-724 (Oct. 28, 2007).

Stoddart, et al., "Single-nucleotide discrimination in immobilized DNA oligonucleotides with a biological nanopore", Proc Natl Acad Sci USA. May 12, 2009;106(19):7702-7. doi: 10.1073/pnas.0901054106. Epub Apr. 20, 2009.

* cited by examiner

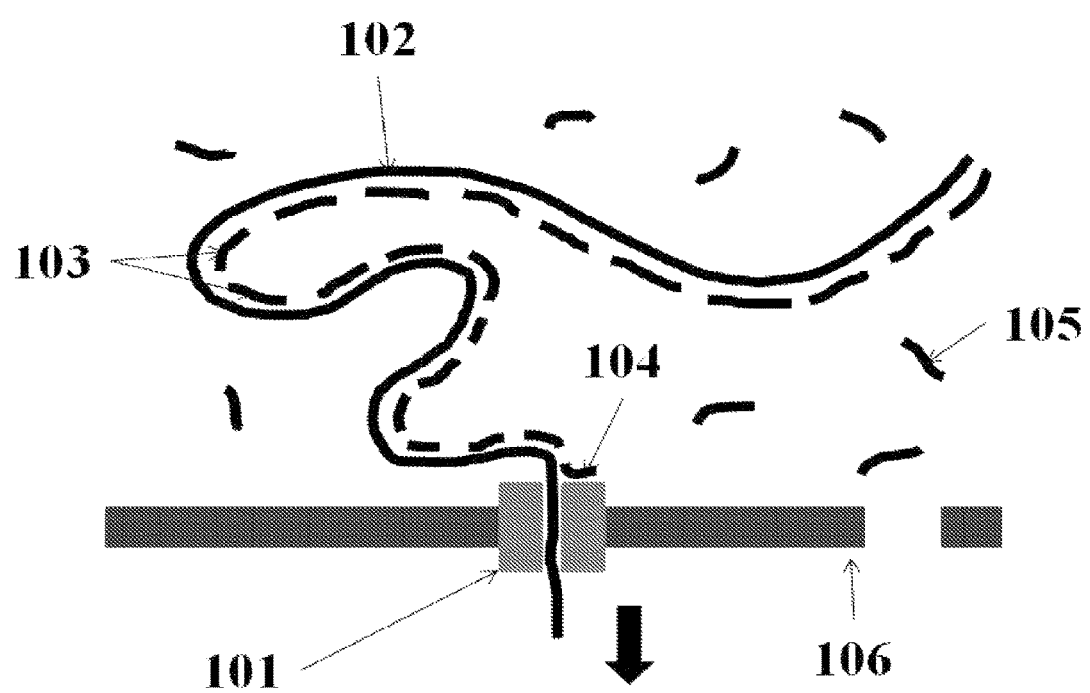

SYSTEMS AND METHODS FOR DETERMINING GENETIC DATA

CROSS-REFERENCE

The present invention is a divisional of U.S. patent application Ser. No. 14/355,203, filed Apr. 29, 2014, now U.S. Pat. No. 10,260,093, which is the U.S. National Phase application of PCT/US2012/063099, filed Nov. 1, 2012, which claims the benefit of U.S. Provisional Application No. 61/554,815, filed Nov. 2, 2011, each of which is incorporated herein by reference in its entirety.

BACKGROUND

At least some next generation sequencing ("NGS") techniques focus on improving sequencing accuracy, increasing throughput, and reducing sequencing costs. Current NGS platforms provide for preparation, detection, imaging, analysis, and/or sequencing of large quantities of complex samples, including nucleic acids from entire genomes in single sequencing processes or instrument runs.

SUMMARY

Systems and methods for polynucleotide sequencing are provided herein. In particular, the presently disclosed systems and methods optimize control, speed, movement, and/or translocation of a sample (e.g., a polynucleotide) within, through, or at least partially through a nanopore (or some type of protein or mutant protein) in order to accumulate sufficient time and current blocking information to uniquely identify contiguous nucleotides in a single-stranded area of a polynucleotide. That is, in some embodiments, oligonucleotide n-mers can be selected and bound to a target polynucleotide so that these double-stranded portions are "stuck" within a portion of the nanopore for a predictable amount of time while a single-stranded portion ("ss") of the target is interrogated and genetic analysis is generated and detected. After an amount of time, the "stuck" oligonucleotide can be melted away and the sample can controllably be translocated through the nanopore. In some embodiments, the oligonucleotide n-mers can be selected such that each oligonucleotide n-mer melts away or is removed at a uniform rate such that the sample moves through the nanopore at a controlled and/or constant rate.

In an aspect, a method for sequencing a nucleic acid sample comprises (a) associating a plurality of oligonucleotide analogs with the nucleic acid sample; and (b) directing the nucleic acid sample through a nanopore, wherein an individual oligonucleotide analog of the plurality of oligonucleotide analogs becomes disassociated from the nucleic acid sample as the sequence of the nucleic acid sample is determined, wherein the plurality of oligonucleotide analogs that are associated with the nucleic acid sample comprise at least about 25% universal bases. In some embodiments, the method further comprises (c) sequencing the nucleic acid sample with the aid of the nanopore.

In some embodiments, the plurality of oligonucleotide analogs that are associated with the nucleic acid sample comprise at least about 50% universal bases. In some embodiments, the plurality of oligonucleotide analogs that are associated with the nucleic acid sample comprise at least about 80% universal bases. In some embodiments, the plurality of oligonucleotide analogs that are associated with the nucleic acid sample are formed entirely of universal bases.

In some embodiments, the individual oligonucleotide analog associates with the nucleic acid sample in a sequence-independent manner.

In some embodiments, the plurality of oligonucleotide analogs further comprise a peptide nucleic acid (PNA), a locked nucleic acid (LNA), a morpholino, or any combination thereof.

In some embodiments, the universal base comprises 5-nitroindole, 3-nitropyrrole, 3-methyl 7-propynyl isocarbostyril (PIM), 3-methyl isocarbostyril (MICS), 5-methyl isocarbostyril (5MICS), or any combination thereof.

In some embodiments, the plurality of oligonucleotide analogs comprises at least 3 universal bases. In some embodiments, the plurality of oligonucleotide analogs comprises at least 5 universal bases. In some embodiments, the plurality of oligonucleotide analogs comprises at least 10 universal bases.

In some embodiments, the plurality of ologinucleotide analogs comprises at least one of adenine (A), cytosine (C), guanine (G), thymine (T) and uricil (U).

In some embodiments, the plurality of oligonucleotide analogs associate with the nucleic acid sample with a melting temperature of at least 30° C.

In some embodiments, the nucleic acid sample is a single-stranded nucleic acid sample.

In some embodiments, the nanopore is in a membrane that is adjacent to a sensing electrode.

In some embodiments, the sensing electrode is coupled to an integrated circuit.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is an embodiment of sequencing a nucleic acid molecule using an oligonucleotide comprising universal bases.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Various aspects of the invention can be implemented in numerous ways, including as a process, an apparatus, a system, a composition of matter, a computer program product embodied on a computer readable storage medium, and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

Nanopore-Based Sequencing

Techniques for manipulating, detecting, characterizing and/or determining the sequence of a molecule (e.g., a nucleic acid molecule) using a nanopore device are described herein. Devices and methods for sequencing nucleic acid molecules can be found in PCT Patent Publication No. WO/2011/097028, PCT Patent Publication No. WO/2012/088339 and PCT Patent Publication No. WO/2012/088341, which are each hereby incorporated by reference in their entirety.

In some instances, a single stranded nucleic acid molecule (e.g., deoxyribonucleic acid (DNA) or ribonucleic acid (RNA)) is passed through a nanopore that is inserted in a membrane in proximity to an electrode and a sensing circuit. The electrode and circuit can monitor the current that passes through the nanopore. As various nucleotide bases (e.g., adenine (A), guanine (G), cytosine (C), thymine (T) and uracil (U)) pass through the nanopore, the current passing through the nanopore can be affected. In some instances, each of the bases affects the current in a unique way (e.g., A differently from G, C, T, and U) and the sequence of the nucleic acid molecule can be determined from the current. The nanopore can be a solid state nanopore or a biological nanopore such as the protein alpha-hemolysin.

In some instances, the nucleic acid molecule passes through the nanopore too quickly to determine individual bases with sufficient accuracy (e.g., at least 95% or at least 99%). In an aspect, described herein are methods for uniformly slowing down the passage of the nucleic acid through the nanopore.

Sequencing Using Universal Bases

Surprisingly, the rate at which the nucleic acid passes through the nanopore can be controlled using oligonucleotide analogs comprising universal bases. Nucleic acid molecules can be sequenced by passing the molecule through a nanopore as described herein, but the rate of nucleic acid passage is often too rapid to determine the nucleic acid sequence accurately and/or to resolve individual nucleic acid positions.

It is known that oligonucleotides can be used to slow the rate at which the nucleic acid passes through the nanopore by the oligonucleotide associating with the nucleic acid strand. With reference to FIG. 1, since double stranded nucleic acid molecules do not pass through the nanopore 101, the passage of a single stranded nucleic acid 102 can be slowed as the portion of the nucleic acid molecule with associated oligonucleotide (which is double stranded at such portions of the nucleic acid, e.g., 103) comes into contact with the nanopore 104. Passage of the nucleic acid through the nanopore can continue after the oligonucleotide is dissociated from the nucleic acid strand 105. In some embodiments, the nanopore is in a membrane 106 that is adjacent to a sensing electrode. The sensing electrode can be coupled to an integrated circuit.

Some embodiments are based on the realization that slowing the rate of nucleic acid passage through the nanopore with oligonucleotides comprising all or nearly all (e.g., greater than 75%) native nucleotides (i.e., A, C, G, T and U) can have certain disadvantages. For example, since oligonucleotides associate in a sequence dependent manner, a large and diverse population of oligonucleotides can be needed to slow the nucleic acid molecule along all portions of its length. Also, sequencing using native oligonucleotides can lead to an inconsistent rate of nucleic acid passage marked by rapid passage punctated by periods of slow passage where oligonucleotides are associated. Some embodiments are based on the unexpected realization that a more continuous rate than afforded by sequencing with native oligonucleotides may be desirable, and such continuously slow rate could be achieved by using oligonucleotides comprising universal bases. In some cases, the rate is constant and/or suitable for identifying individual nucleotide positions of a nucleic acid.

The term "free flow" in some cases refers to the unimpeded progression of a molecule from one point to another (e.g., through a nanopore). In some situations, the rate at which a molecule (e.g., nucleic acid molecule) passes through a nanopore may be slowed or otherwise decreased with respect to the rate at which the molecule freely passes through ("free flow") the nanopore. The rate may be continuously slowed. In some examples, the rate of progression of a molecule through a nanopore is slowed with the aid of universal bases.

Universal bases can be nucleobases that associate with a nucleic acid strand in a sequence-independent manner. In some cases, universal bases are capable of pairing with each of A, C, T and G. Universal bases are hydrophobic in some instances. The association between a universal base and a nucleic acid can be weaker (lower melting temperature) than the base-pair associations between A with T and G with C. In some embodiments, universal bases do not form hydrogen bonds with A, C, T or G. In some cases, universal bases have a size, shape and charge suitable for stacking with nucleic acids.

Universal bases generally lack hydrogen bonding sites and are generally hydrophobic aromatic "base" residues. Some of their effects derive from their ability to stack within a duplex and from their hydrophobic character. The universal bases can be incorporated into DNA as their phosphoramidite derivatives. In some embodiments, desirable features for a universal base can include one or more of the following: (i) pair with all the natural bases equally when opposite them in an oligonucleotide duplex; (ii) form a duplex which primes DNA synthesis by a polymerase; (iii) direct incorporation of the 5'-triphosphate of each of the natural nucleosides opposite it when copied by a polymerase; (iv) be a substrate for polymerase as the 5'triphosphate; and (v) be recognized by intracellular enzymes such that DNA containing them may be cloned. In some embodiments, the universal bases can be selecting by determining those universal bases optimized for nanopore sequencing.

In some embodiments, the oligonucleotide analogs can rely entirely or substantially entirely on base-stacking energetics for hybridization. A potential advantage of this approach is that high concentration of oligonucleotide analogs and low temperatures of operation (e.g., of a nanopore sequencing system, such as 20° C.-30° C.) can be utilized to drive this hybridization process.

The universal bases can be any suitable base, including combinations of a plurality of different bases. The universal bases can be polymerized into a linear chain to form an oligonucleotide analog. Oligonucleotide analogs are any polymerized nucleotide that comprises a non-native base (i.e., other than A, C, T, G or U).

In some instances, the universal base is 5-nitroindole, or a derivative or substitution thereof. The universal base 5-nitroindole is represented by the chemical structure:

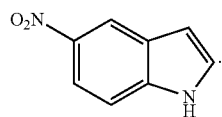

One potential benefit of utilizing 5-nitroindole is its effectiveness as a primer, including when the oligonucleotide has consecutive 5-nitroindoles.

In some instances, the universal base is 3-nitropyrrole, or a derivative or substitution thereof. The universal base 3-nitropyrrole is represented by the chemical structure:

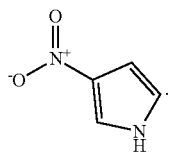

In some instances, the universal base is 3-methyl 7-propynyl isocarbostyril (PIM), or a derivative or substitution thereof. The universal base 3-methyl 7-propynyl isocarbostyril (PIM) is represented by the chemical structure:

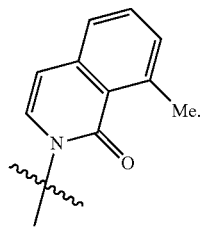 [SMILES: *n1ccc2cccc(C)c2c1=O]

In some instances, the universal base is 3-methyl isocarbostyril (MICS), or a derivative or substitution thereof. The universal base 3-methyl isocarbostyril (MICS) is represented by the chemical structure:

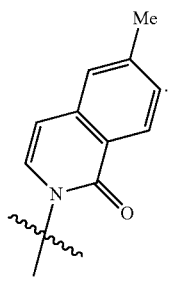 [SMILES: *n1ccc2cc(C)ccc2c1=O]

In some instances, the universal base is 5-methyl isocarbostyril (5MICS), or a derivative or substitution thereof. The universal base 5-methyl isocarbostyril (5MICS) is represented by the chemical structure:

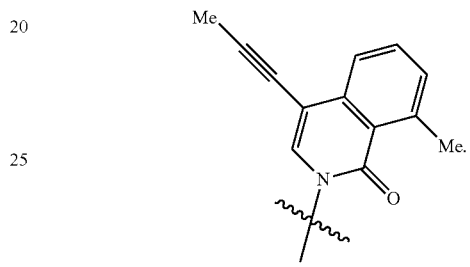

In an aspect, a method for sequencing a nucleic acid sample comprises (a) associating a plurality of oligonucleotide analogs with the nucleic acid sample; and (b) directing the nucleic acid sample through a nanopore. An individual oligonucleotide analog of the plurality of oligonucleotide analogs becomes disassociated from the nucleic acid sample as the sequence of the nucleic acid sample is determined. In some embodiments, the method further comprises (c) sequencing the nucleic acid sample with the aid of the nanopore.

The plurality of oligonucleotide analogs that are associated with the nucleic acid sample can comprise any suitable percentage of universal bases. In some embodiments, the oligonucleotide analogs comprise about 20%, about 30%, about 40%, about 50%, about 60%, about 70%, about 80%, about 90%, about 95%, or 100% universal bases. In some embodiments, the oligonucleotide analogs comprise at least about 20%, at least about 30%, at least about 40%, at least about 50%, at least about 60%, at least about 70%, at least about 80%, at least about 90%, or at least about 95% universal bases.

The plurality of oligonucleotide analogs that are associated with the nucleic acid sample can comprise any suitable number of universal bases. In some embodiments, the oligonucleotide analogs comprise about 3, about 5, about 7, about 10, about 15, about 20, about 25, about 30, about 35, about 40, about 45, about 50, about 60, about 70, about 80, or about 100 universal bases. In some embodiments, the oligonucleotide analogs comprise at least about 3, at least about 5, at least about 7, at least about 10, at least about 15, at least about 20, at least about 25, at least about 30, at least about 35, at least about 40, at least about 45, at least about 50, at least about 60, at least about 70, at least about 80, or at least about 100 universal bases.

In some embodiments, the oligonucleotides comprising universal bases can be formed entirely or at least substantially entirely of analogue bases so that n-mer "sets" could be synthesized in bulk, e.g., 5-mers, 6-mers, . . . 10-mers could each be synthesized in a single manufacturing run.

The individual oligonucleotide analogs can associate with the nucleic acid sample in a sequence-independent manner. In some instances, the oligonucleotide analogs comprise at least one of adenine (A), cytosine (C), guanine (G), thymine (T) or uricil (U) (i.e., native bases). Oligonucleotide analogs with at least one native base can associate with the nucleic acid sample in a sequence-dependent manner by base pairings between the nucleic acid sample and the native bases of the oligonucleotide. Such base pairings can increase the melting temperature and/or strength of association of the oligonucleotide to the sample, optionally with enough base pairing degeneracy such that the rate at which the nucleic acid passes through the nanopore is suitably slow and consistent.

The plurality of oligonucleotide analogs that are associated with the nucleic acid sample can comprise any suitable percentage of native bases. In some embodiments, the oligonucleotide analogs comprise about 3%, about 5%, about 7%, about 10%, about 15%, about 20%, about 25%, about 30%, about 40%, or about 50% native bases. In some embodiments, the oligonucleotide analogs comprise at least about 3%, at least about 5%, at least about 7%, at least about 10%, at least about 15%, at least about 20%, at least about 25%, at least about 30%, at least about 40%, or at least about 50% native bases.

The plurality of oligonucleotide analogs that are associated with the nucleic acid sample can comprise any suitable number of native bases. In some embodiments, the oligonucleotide analogs comprise about 3, about 5, about 7, about 10, about 15, about 20, about 25, or about 30 native bases. In some embodiments, the oligonucleotide analogs comprise at least about 3, at least about 5, at least about 7, at least about 10, at least about 15, at least about 20, at least about 25, or at least about 30 native bases.

The oligonucleotides can associate with the nucleic acid molecule with any suitable strength. In some cases, the strength of association is represented by a melting temperature (e.g., the temperature at which the oligonucleotide becomes dissociated from the nucleic acid). In some embodiments, the plurality of oligonucleotide analogs associate with the nucleic acid sample with a melting temperature of about 20° C., about 30° C., about 40° C., about 50° C., about 60° C., about 70° C., about 80° C. or about 90° C. In some embodiments, the plurality of oligonucleotide analogs associate with the nucleic acid sample with a melting temperature of at least about 20° C., at least about 30° C., at least about 40° C., at least about 50° C., at least about 60° C., at least about 70° C., at least about 80° C. or at least about 90° C.

The oligonucleotide analogs can further comprise modifications other than universal bases. In some cases, the oligonucleotide analogs are peptide nucleic acids (PNA). PNA has a linkage backbone different than that of a nucleic acid and is somewhat of a misnomer as PNA is not an acid.

DNA and RNA have a deoxyribose and ribose sugar backbone, respectively, whereas PNA's backbone is composed of repeating N-(2-aminoethyl)-glycine units linked by peptide bonds. The various bases (e.g., purines and pyrimidines) are linked to the backbone by methylene carbonyl bonds. PNAs are depicted like peptides, with the N-terminus at the first (left) position and the C-terminus at the last (right) position. In some cases, the structure of PNA is as seen here:

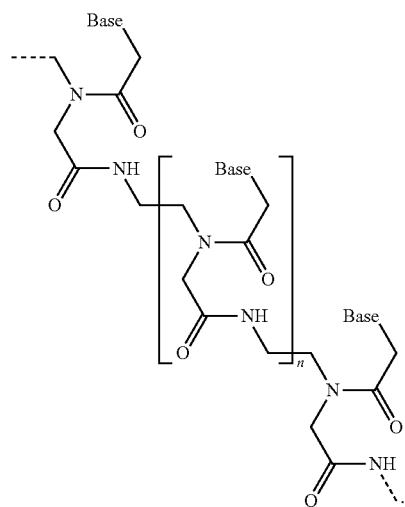

PNA molecules can associate with nucleic acid molecules using the same base-pair recognition chemistry as DNA (e.g., A associating with T and C associating with G), however the strength of association can be different. The binding between PNA and DNA strands can be stronger than between DNA and DNA. In some instances this is thought to be because PNA contains no charged phosphate groups and does not have an electrostatic repulsion with the DNA. In an embodiment, the $T_m$ ("melting" temperature) of a 6-base thymine PNA/adenine DNA double helix is 31° C. in comparison to an equivalent 6-base DNA/DNA duplex that denatures at a temperature less than 10° C.

In some cases, the oligonucleotide analog is PNA comprising universal bases. The oligonucleotide analog can be short (e.g., less than 20 bases, less than 10 bases or less than 6 bases). In some cases, PNA oligomers show greater specificity in binding to complementary DNAs, with a PNA/DNA base mismatch being more destabilizing than a similar mismatch in a DNA/DNA duplex. In some embodiments, PNAs are not easily recognized by either nucleases or proteases, making them resistant to enzyme degradation. In some instances, PNAs are also stable over a wide pH range.

In some cases, the oligonucleotide analogs comprise locked nucleic acids (LNA). LNA is a modified RNA nucleotide and is also referred to as "inaccessible RNA". The ribose moiety of an LNA nucleotide is modified with an extra bridge connecting the 2' oxygen and 4' carbon. The bridge "locks" the ribose in the 3'-endo (North) conformation. In some cases, the structure of PNA is as seen here:

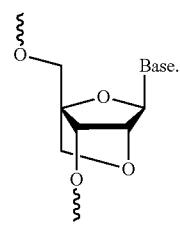

LNA nucleotides can be mixed with DNA or RNA residues in the oligonucleotide as desired. Such oligomers are synthesized chemically and are commercially available. The locked ribose conformation enhances base stacking and backbone pre-organization. This significantly increases the hybridization strength (melting temperature) of oligonucleotides.

LNA nucleotides are used to increase the sensitivity and specificity of expression in DNA microarrays, FISH probes, real-time PCR, probes and other molecular biology techniques based on oligonucleotides. In some embodiments, the oligonucleotide analogs comprise locked nucleic acids comprising universal bases.

In some cases, the oligonucleotide analogs comprise morpholinos. Structurally, the difference between morpholinos and nucleic acids is that bases are bound to morpholine rings instead of deoxyribose rings (in the case of DNA) and linked through phosphorodiamidate groups instead of phosphates. This may be visualized by referring to the structure as follows:

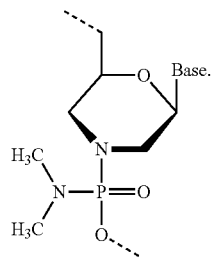

Replacement of anionic phosphates with the uncharged phosphorodiamidate groups can eliminate ionization in some pH ranges (e.g., ranges where nucleic acid sequencing is performed such as between 6.0 and 8.0), so morpholinos can be uncharged molecules. In some instances, morpholinos bind to nucleic acid molecules with a stronger affinity (higher melting temperature) than the binding of nucleic acid to nucleic acid. Morpholinos can comprise natural bases (e.g., A, C, G, T and/or U) and/or universal bases as described herein. Because of their unnatural backbones, morpholinos are generally not recognized and/or degraded by cellular proteins such as nucleases.

In an aspect, a method for sequencing a nucleic acid molecule comprises (a) associating a plurality of oligonucleotide analogs with the nucleic acid molecule; and (b) passing the nucleic acid molecule through a nanopore. Passing the nucleic acid molecule through the nanopore can disassociate the oligonucleotide analogs from the nucleic acid molecule. In some embodiments, the method further comprises (c) sequencing the nucleic acid molecule with the aid of the nanopore.

The nucleic acid molecule can be passed through the nanopore at any suitable rate. In some embodiments, the nucleic acid molecule is passed through a nanopore at a rate that allows for sequencing individual nucleic acid bases of the nucleic acid molecule.

The rate at which the nucleic acid sample passes through the nanopore can be uniformly slowed down. A "uniform" rate has a low variability and is not characterized by stops and starts. The standard deviation of the rate can be compared with the average rate over a certain time period to determine whether the rate is uniform in some cases. The time period is sufficiently long, such as the time period required to sequence at least 1000, at least 10000 or at least 1000000 nucleic acid bases. Those skilled in the art know how to calculate averages and standard deviations. In some embodiments, the standard deviation of the rate at which the nucleic acid molecule passes through the nanopore is about 1%, about 5%, about 10%, about 20%, about 30%, about 40%, about 50%, or about 60% of the average rate at which the nucleic acid molecule passes through the nanopore. In some cases, the standard deviation of the rate at which the nucleic acid molecule passes through the nanopore is less than about 1%, less than about 5%, less than about 10%, less than about 20%, less than about 30%, less than about 40%, less than about 50%, or less than about 60% of the average rate at which the nucleic acid molecule passes through the nanopore.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for sequencing a single stranded nucleic acid molecule, the system comprising:
   (a) a nucleic acid molecule comprising a plurality of single stranded regions and a plurality of double stranded regions, wherein:
      (a1) each of the plurality of double stranded regions has a melting temperature of at least 30° C., and is formed by hybridizing a portion of the plurality of single stranded regions to an oligonucleotide analog from a plurality of oligonucleotide analogs comprising at least about 25% universal bases; and
      (a2) each of the plurality of single stranded regions comprises a portion that does not hydbridize to the oligonucleotide analog; and
   (b) a nanopore that permits passage of each of the plurality of single stranded regions of the nucleic acid molecule and does not permit passage of each of the plurality of double stranded regions of the nucleic acid molecule;
   (c) a sensing electrode adjacent to the nanopore, such that the sensing electrode is capable of monitoring a current that passes through the nanopore, wherein the universal bases are capable of pairing with each of A, C, T and G in a sequence-independent manner.

2. The system of claim 1, wherein the at least about 25% universal bases comprises at least about 50% of the universal bases.

3. The system of claim 1, wherein the at least about 25% universal bases comprises at least about 80% of the universal bases.

4. The system of claim 1, wherein the oligonucleotide analogs further comprise a peptide nucleic acid (PNA), a locked nucleic acid (LNA), a morpholino, or any combination thereof.

5. The system of claim 1, wherein the universal base comprises 5-nitroindole, 3-nitropyrrole, 3-methyl 7-propynyl isocarbostyril (PIM), 3-methyl isocarbostyril (MICS), 5-methyl isocarbostyril (SMICS), or any combination thereof.

6. The system of claim 1, wherein the at least about 25% universal bases comprise at least 3 of the universal bases.

7. The system of claim 1, wherein the at least about 25% universal bases comprise at least 5 of the universal bases.

8. The system of claim 1, wherein the at least about 25% universal bases comprise at least 10 of the universal bases.

9. The system of claim 1, wherein the plurality of oligonucleotide analogs comprises at least one of adenine (A), cytosine (C), guanine (G), thymine (T) and uracil (U).

10. The system of claim 1, wherein the nanopore is in a membrane that is adjacent to the sensing electrode.

11. The system of claim 1, wherein the sensing electrode is coupled to an integrated circuit.

* * * * *